United States Patent [19]
Cox et al.

[11] Patent Number: 5,354,920
[45] Date of Patent: Oct. 11, 1994

[54] CHEMICAL PROCESS FOR THE PREPARATION OF A 2-HYDROXYARYLALDEHYDE

[75] Inventors: Brian G. Cox, Poynton; Daniel Levin, Manchester, both of United Kingdom

[73] Assignee: Zeneca Limited, London, England

[21] Appl. No.: 103,697

[22] Filed: Aug. 10, 1993

[30] Foreign Application Priority Data

Aug. 20, 1992 [GB] United Kingdom ............... 9217723

[51] Int. Cl.$^5$ .............................................. C07C 45/00
[52] U.S. Cl. ................................ 568/437; 568/426; 568/432; 568/433
[58] Field of Search ............... 568/426, 437, 432, 433

[56] References Cited

FOREIGN PATENT DOCUMENTS

| | | | |
|---|---|---|---|
| 434249 | 6/1991 | European Pat. Off. | 568/437 |
| 529870 | 3/1993 | European Pat. Off. | 568/437 |
| 3052839 | 3/1991 | Japan | 563/437 |
| 2104516 | 3/1983 | United Kingdom | 568/437 |

Primary Examiner—Werren B. Lone
Attorney, Agent, or Firm—Cushman, Darby & Cushman

[57] ABSTRACT

A method for the preparation of a 2-hydroxyarylaldehyde which comprises reacting an aryloxymagnesium halide derived from a phenol having at least one free ortho position relative to the phenolic hydroxy group with formaldehyde or a formaldehyde-liberating compound under substantially anhydrous conditions in the presence of a polar organic solvent other than hexamethylphosphoramide or 1,3-dimethyl-3,4,5,6-2(1H)-pyrimidone.

14 Claims, No Drawings

CHEMICAL PROCESS FOR THE PREPARATION OF A 2-HYDROXYARYLALDEHYDE

This invention relates to a chemical process and more particularly to a method for the preparation of 2-hydroxyarylaldehydes.

A number of 2-hydroxyarylaldehydes are known as useful products in the perfume and agricultural chemical industries and especially as intermediates for the corresponding oximes which are used as metal extractants.

Methods that have been described for the production of 2-hydroxyarylaldehydes have included, in particular, the ortho-formylation of a phenol using formaldehyde or a formaldehyde-liberating compound in the presence of a suitable ortho-selective catalyst, the reaction generally being performed at an elevated temperature in an anhydrous organic solvent. Catalysts proposed for this reaction include tin, chromium, iron, titanium, zirconium and aluminium compounds, often with the additional use of a nitrogen base as catalyst promoter. In this connection, reference can be made to GB-A-2163157, U.S. Pat. No. 4231967, EP-A-0077279 and EP-A-0106653. Whilst these processes can give good yields of hydroxy-aldehyde, many of the catalysts and/or promoters used are costly and/or toxic materials requiring special handling on an industrial scale. Additionally, some of the processes require the use of pressure.

In J.C.S. Perkin I, 1978, 313, Casiraghi et al describe the reaction of formaldehyde with aryloxymagnesium bromides to give 2,2-dihydroxydiphenylmethanes and with aryloxymagnesium bromide-hexamethylphosphoramide 1:1 complexes to give 2-hydroxybenzaldehydes, the reaction being performed in refluxing benzene. Whilst this process gives 2-hydroxybenzaldehydes in high yield and selectivity, Casiraghi et al have acknowledged in a subsequent paper (J.C.S. Perkin I, 1980, 1852) that "the need to use a considerable amount of toxic hexamethylphosphoramide" is a factor seriously limiting its applicability on a large scale.

In EP-A-0434249, there is described a method of making 5-methylsalicylaldehyde by reacting 4-methylphenoxymagnesium bromide with paraformaldehyde in the presence of 1,3-dimethyl-3,4,5,6-2(1H)-pyrimidone, the latter (also known as DMPU) being specifically recommended in the literature (for example Helv. Chim. Acta, 65, 385, 1982 and Chem. Ber., 115, 1705, 1982) as a safer substitute for the carcinogenic hexamethylphosphoramide.

It has now been found that other low cost, low toxicity polar solvents may be used in place of hexamethylphosphoramide or DMPU for the production of 2-hydroxyarylaldehydes from aryloxymagnesium halides.

Thus, according to the invention, there is provided a method for the preparation of a 2-hydroxyarylaldehyde which comprises reacting an aryloxymagnesiumhalide derived from a phenol having at least one free ortho position relative to the phenolic hydroxy group with formaldehyde or a formaldehyde-liberating compound under substantially anhydrous conditions in the presence of a polar organic solvent other than hexamethylphosphoramide or 1,3-dimethyl-3,4,5,6-2(1H)-pyrimidone.

The reaction on which the method of the invention is based is suitably performed at temperatures within the range from about 60° to about 130° C., for example 80°–120° C. Somewhat lower reaction temperatures can also be used but will generally result in longer reaction times whilst higher reaction temperatures may lead to increased side reactions and, therefore, to a less pure product. The reaction is preferably carried out at atmospheric pressure but lower or higher pressures may be employed if desired. By-products of the reaction, for example methanol, methyl formate and methylal, may be removed from the reaction mixture as they are formed, using conventional procedures.

The substantially anhydrous conditions required by the reaction may be conveniently provided by the use of substantially anhydrous reactants together with a substantially anhydrous solvent system and conventional techniques, for example distillation, for removal of adventitious moisture. Suitable solvent systems typically comprise an inert non-polar or low polarity organic solvent used in conjunction with the aforementioned polar organic solvent.

Suitable inert solvents will be liquids at the reaction temperature and will act as solvents for the aryloxymagnesium halide. Preferably, they will allow removal of one or more of the volatile by-products by distillation. Examples of suitable inert solvents include aromatic hydrocarbons, for example toluene, xylene, mesitylene, cumene, cymene, tetralin and, especially, toluene and chlorinated aromatic hydrocarbons, for example chlorobenzene and o-dichlorobenzene. Mixtures of inert solvents may be used.

Suitable polar solvents will be liquids at the reaction temperature and will include compounds capable of acting as ligands with respect to magnesium atoms. Such compounds include polar aprotic solvents such as dimethylsulphoxide, sulpholane, dimethylacetamide, N-formylpiperidine, N-methylpyrrolidinone, tetramethylurea and, especially, dimethylformamide, tertiary bases such as triethylamine, tri-octylamine, tetramethylethylenediamine and pyridine, ethers such as diethyl ether, diphenyl ether, tetrahydrofuran, glyme, diglyme, triglyme, tris[2-(2-methoxyethoxy)ethyl]amine and crown ethers and other polar solvents such as "Polymeg" 1000 and "Cellosolve" and the like. Particularly useful polar solvents include lower alkanols such as ethanol and, especially, methanol. Mixtures of polar solvents may be used.

Aryloxymagnesium halides which may be used in the method of the invention may be obtained by conventional methods. Especially useful aryloxymagnesium halides include phenoxymagnesium chlorides, bromides and iodides wherein the phenoxy residues may be unsubstituted or may be substituted in any or all of the positions, other than both the 2- and 6-positions, by substituents which do not interfere with the course of the reaction and which preferably are electron-repelling or weakly electron-attracting.

The invention is especially concerned with the use of phenoxymagnesium halides derived from phenols of the formula:

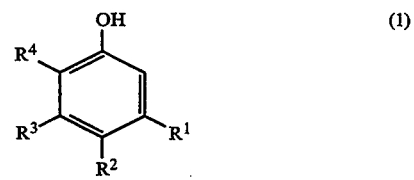

(1)

wherein each of $R^1$, $R^2$, $R^3$ and $R^4$, independently, represents a hydrogen or halogen atom or an alkyl, cycloalkyl, aralkyl, aryl, alkaryl, alkoxy, aryloxy, acyl or hydroxy group, for the preparation of 2-hydroxyarylaldehydes of the formula:

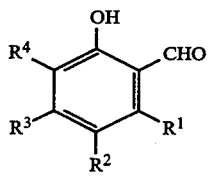
(2)

Each of the various hydrocarbyl, hydrocarbyloxy and acyl groups which may be represented by $R^1$, $R^2$, $R^3$ and $R^4$ suitably contains up to 36 carbon atoms, for example from 5 to 22 carbon atoms.

Particular mention may be made of phenoxymagnesium halides derived from phenols of the formula:

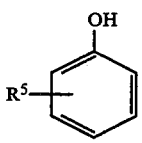
(3)

wherein $R^5$ represents hydrogen or a $C_{1-22}$-alkyl radical said compounds being used in the preparation of 2-hydroxyarylaldehydes of the formula:

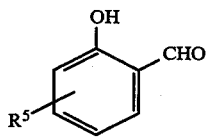
(4)

Preferably, $R^5$ is a C7-12-alkyl radical, especially in the 4-position relative to the hydroxyl group.

The formaldehyde used in the method of the invention may be in the form of free gaseous formaldehyde or a solution in an anhydrous solvent or a formaldehyde-liberating compound, that is to say a compound capable of liberating formaldehyde under the conditions employed in the method of the invention. Suitable formaldehyde-liberating compounds include polymeric forms of formaldehyde such as paraformaldehyde. It is preferred to add the formaldehyde or formaldehyde-liberating compound gradually (continuously or discontinuously) to the aryloxymagnesium halide in the solvent system.

The formaldehyde or formaldehyde-liberating compound is generally employed in the method of the invention in an amount of at least two moles, expressed as formaldehyde (HCHO), per mole of aryloxymagnesium halide. Typical ratios are from 2.5 to 5, preferably from 2.5 to 4 moles of formaldehyde per mole of aryloxymagnesium halide. The polar solvent is suitably used in an amount of from 1 to 2 moles per mole of aryloxymagnesium halide but larger amounts may be used if desired. Since methanol is a by-product of the reaction, conversion and yield may be maximised by removing this methanol and any other volatile by-products by distillation during the course of the reaction so as to maintain the polar solvent/aryloxymagnesium halide ratio at the optimum level.

At the end of the reaction, the 2-hydroxyarylaldehyde product may be isolated from the reaction mixture using conventional methods. Thus, the cooled reaction mixture may be drowned into cold dilute acid and the aqueous mixture may then be extracted with a suitable organic solvent such as toluene which may then be removed by distillation leaving the crude 2-hydroxyarylaldehyde which may be subjected to further conventional purification as desired.

The method of the invention is particularly suitable for use in the preparation of 5-alkylsalicylaldehydes of the formula:

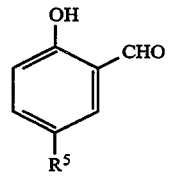
(5)

wherein $R^5$ is as defined above, from the corresponding 4-alkylphenoxy magnesium halides. Thus, 4-nonylphenol (a mixture of isomers derived from phenol and propylene trimer) may be converted to the corresponding 4-nonylphenoxy magnesium halide which may be used in the method of the invention to prepare 5-nonylsalicylaldehyde, an intermediate in the manufacture of the metal extractant 5-nonylsalicylaldoxime.

The invention is illustrated but not limited by the following Examples.

EXAMPLE 1

Diethyl ether (100 ml) and 4-nonylphenol (11.2 g) were charged to a dry flask, stirred under a nitrogen atmosphere and cooled to 0° C. Ethyl magnesium bromide (18 ml of a 3M solution in diethyl ether) was added slowly from a syringe, keeping the temperature below 10° C. The reaction mixture was stirred for a further ½ hour, warming to room temperature. Diethyl ether was distilled off, toluene (100 ml) was added and distillation was continued until an internal temperature of 105° C. had been reached.

After cooling the reaction mixture to 90° C., triethylamine (30 ml) was added followed by the slow addition of a slurry of paraformaldehyde (6 g) in toluene (12 ml), the temperature being maintained at 95° C.

After stirring at 95°–100° C. for 4 hours, the reaction mixture was drowned into a mixture of cold water (500 ml) and 98% sulphuric acid (12 g). The mixture was stirred for 2 hours, then filtered and the organic layer separated from the aqueous layer. The organic layer was then washed with water till acid-free and the toluene was removed in a rotary evaporator leaving 5-nonylsalicylaldehyde (13.2 g at 76% strength, yield 80.9).

EXAMPLE 2

The procedure described in Example 1 was repeated but with the replacement of triethylamine (30 ml) by pyridine (30 ml). The product comprised 5-nonylsalicylaldehyde (12.4 g at 87.3% strength, yield 87.3%).

EXAMPLE 3

The procedure described in Example 1 was repeated but with the replacement of triethylamine (30 ml) by diglyme (30 ml). The product comprised 5-nonylsalicylaldehyde (12.5 g at 67.0% strength, yield 67.5%).

EXAMPLE 4

The procedure described in Example 1 was repeated but with the replacement of triethylamine ( 30 ml ) by tetramethyl ethylene diamine (30 ml). The product comprised 5-nonylsalicylaldehyde (12.7 g at 83.4% strength, yield 85.4%).

EXAMPLE 5

The procedure described in Example 1 was repeated but with the replacement of triethylamine (30 ml) by N-methylpyrrolidinone (30 ml). The product comprised 5-nonylsalicylaldehyde in high yield.

EXAMPLE 6

The procedure described in Example 1 was repeated but with the replacement of triethylamine (30 ml) by dimethylformamide (11.1 g). The product comprised 5-nonylsalicylaldehyde in 65.5% yield.

EXAMPLE 7

The procedure described in Example 1 was repeated but with the replacement of triethylamine (30 ml) by methanol (30 ml). The product comprised 5-nonylsalicylaldehyde (13.3 g at 64.6% strength, yield 69.3%).

EXAMPLE 8

Ethylmagnesium bromide (18 ml of 3M solution in diethyl ether) was added dropwise to a stirred solution of 4-nonylphenol (11.2 g) in diethyl ether (100 ml) at 0°–10° C. under nitrogen. Stirring was continued at 10° C. for 30 minutes, the mixture was allowed to warm to ambient temperature, the bulk of the diethyl ether was removed by distillation, toluene (100 ml) and methanol (6.5 g) were added and removal of diethyl ether and free (uncoordinated to Mg) methanol was continued by fractional distillation with vigorous stirring until the temperature of the mixture rose to 100°–105° C. The mixture was cooled to 95° C. and a slurry of paraformaldehyde (6 g) in toluene (12 ml) was added dropwise over 20 minutes, the temperature of the reaction mixture being maintained at 95°–100° C. with removal of volatile by-products by distillation. Stirring was continued at 95°–100° C. for 2 hours, the mixture was added to a cold stirred solution of sulphuric acid (12 g of 98% strength material) in water (500 ml) at 10° C., the resulting mixture was stirred at 20°–30° C. for 2 hours, the mixture was filtered and the upper organic layer separated from the lower aqueous layer. The organic layer was washed with water (3×50 ml) and solvent was removed by evaporation under reduced pressure to give crude 2-hydroxy-5-nonylbenzaldehyde.

We claim:

1. A method for the preparation of a 2-hydroxyarylaldehyde of the formula:

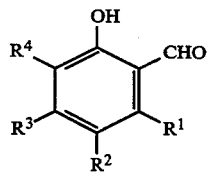

wherein each of $R^1$, $R^2$, $R^3$ and $R^4$, independently, represents hydrogen, halogen, hydroxy or an alkyl, cycloalkyl, aralkyl, aryl, alkaryl, alkoxy or acyl group containing up to 36 carbon atoms which comprises reacting an aryloxymagnesium halide wherein the aryloxy group has the formula:

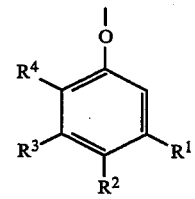

with formaldehyde or a formaldehyde-liberating compound under substantially anhydrous conditions in the presence of a polar organic solvent other than hexamethylphosphoramide or 1,3-dimethyl-3,4,5,6-2(1H)-pyrimidone.

2. A method according to claim 1 wherein the polar organic solvent is used in conjunction with an inert non-polar or low polarity organic solvent.

3. A method according to claim 2 wherein the inert organic solvent comprises an aromatic hydrocarbon or a chlorinated aromatic hydrocarbon.

4. A method according to claim 3 wherein the aromatic hydrocarbon comprises toluene or xylene.

5. A method according to any one of claims 1 to 4 wherein the polar organic solvent comprises a polar aprotic solvent or a lower alkanol.

6. A method according to claim 5 wherein the lower alkanol comprises methanol.

7. A method according to claim 5 wherein the polar aprotic solvent comprises N-methylpyrrolidinone, dimethylformamide, a tertiary base or an ether.

8. A method according to claim 1 wherein each of the alkyl, cycloalkyl, aralkyl, aryl, alkaryl, alkoxy, aryloxy or acyl groups which may be represented by $R^1$, $R^2$, $R^3$ and $R^4$ contains from 5 to 22 carbon atoms.

9. A method according to claim 1 wherein the aryloxymagnesium halide is derived from a phenol of the formula:

wherein $R^5$ represents hydrogen or a $C_{1-22}$-alkyl radical.

10. A method according to claim 9 wherein $R^5$ is a $C_{7-12}$-alkyl radical.

11. A method according to claim 1 wherein the formaldehyde-liberating compound is paraformaldehyde.

12. A method according to claim 1 wherein the amount of formaldehyde or formaldehyde-liberating compound used is at least 2 moles HCHO per mole of aryloxymagnesium halide, 13. A method according to claim 12 wherein the molar ratio of formaldehyde to aryloxymagnesium halide is from 2.5 to 5.

14. A method according to any one of claim 1 wherein the aryloxymagnesium halide is a 4-nonylphenoxymagnesium halide.

* * * * *